United States Patent [19]
Behbehani et al.

[11] Patent Number: 5,953,713
[45] Date of Patent: Sep. 14, 1999

[54] METHOD AND APPARATUS FOR TREATMENT OF SLEEP DISORDER BREATHING EMPLOYING ARTIFICIAL NEURAL NETWORK

[75] Inventors: Khosrow Behbehani, Arlington; John R. Burk, Aledo, both of Tex.; Francisco J. Lopez, Bonita, Calif.; Edgar A. Lucas, Fort Worth, Tex.

[73] Assignee: Board of Regents, The University of Texas System, Austin, Tex.

[21] Appl. No.: 08/928,791

[22] Filed: Sep. 12, 1997

Related U.S. Application Data

[63] Continuation of application No. 08/548,424, Oct. 26, 1995.

[51] Int. Cl.$^6$ ........................................................ G06E 1/00
[52] U.S. Cl. ................................ 706/16; 706/15; 706/19; 706/23; 607/2
[58] Field of Search ............................ 706/15, 62; 607/2

[56] References Cited

U.S. PATENT DOCUMENTS

| | | | |
|---|---|---|---|
| 5,058,600 | 10/1991 | Schechter et al. | 128/716 |
| 5,309,921 | 5/1994 | Kisner et al. | 128/719 |
| 5,458,137 | 10/1995 | Axe et al. | 128/204.23 |
| 5,503,161 | 4/1996 | Van Den Heuvel | 128/773 |

OTHER PUBLICATIONS

"Snore Detection Using A Neural Network" Masters Thesis of Francisco Javier Lopez, Aug. 1994.

Navabi, Mohammad J., et al. "Integrated Monitoring Can Detect Critical Events and Improve Alram Accuracy," Journal of Clinical Engineering, vol. !6, No. 4, Jul.

Lopez et al, "An artificial neural network based snore detector"; Proceedings of the 16th annual international conference of the IEEE engineering in medicine and biology society, pp. 1107–1108 vol. 2, Nov. 1994.

Barschdorff, Dieter et al., "Neural Network Based Multi Sensor Heart Sound Analysis", Computers i n Cardiology, IEEE Press, pp. 303–306, 1991.

*Primary Examiner*—Tariq R. Hafiz
*Assistant Examiner*—Wilbert Starks
*Attorney, Agent, or Firm*—Dan Venglarik

[57] ABSTRACT

A method and apparatus for treating sleep disorder breathing is disclosed having improved ability to accurately detect pharyngeal wall vibration or other apneic events. An interface or mask is placed over a patient's airway. The interface is coupled to a source of pressurized gas. A respiration-related variable, namely the total pressure in the interface, is measured or sampled. The respiration-related variable is input into an artificial neural network trained to recognize patterns characterizing sleep disorder breathing. Responsive to recognition by the artificial neural network of sleep disorder breathing, pressurized gas is supplied to the patient's airways through the interface.

17 Claims, 5 Drawing Sheets

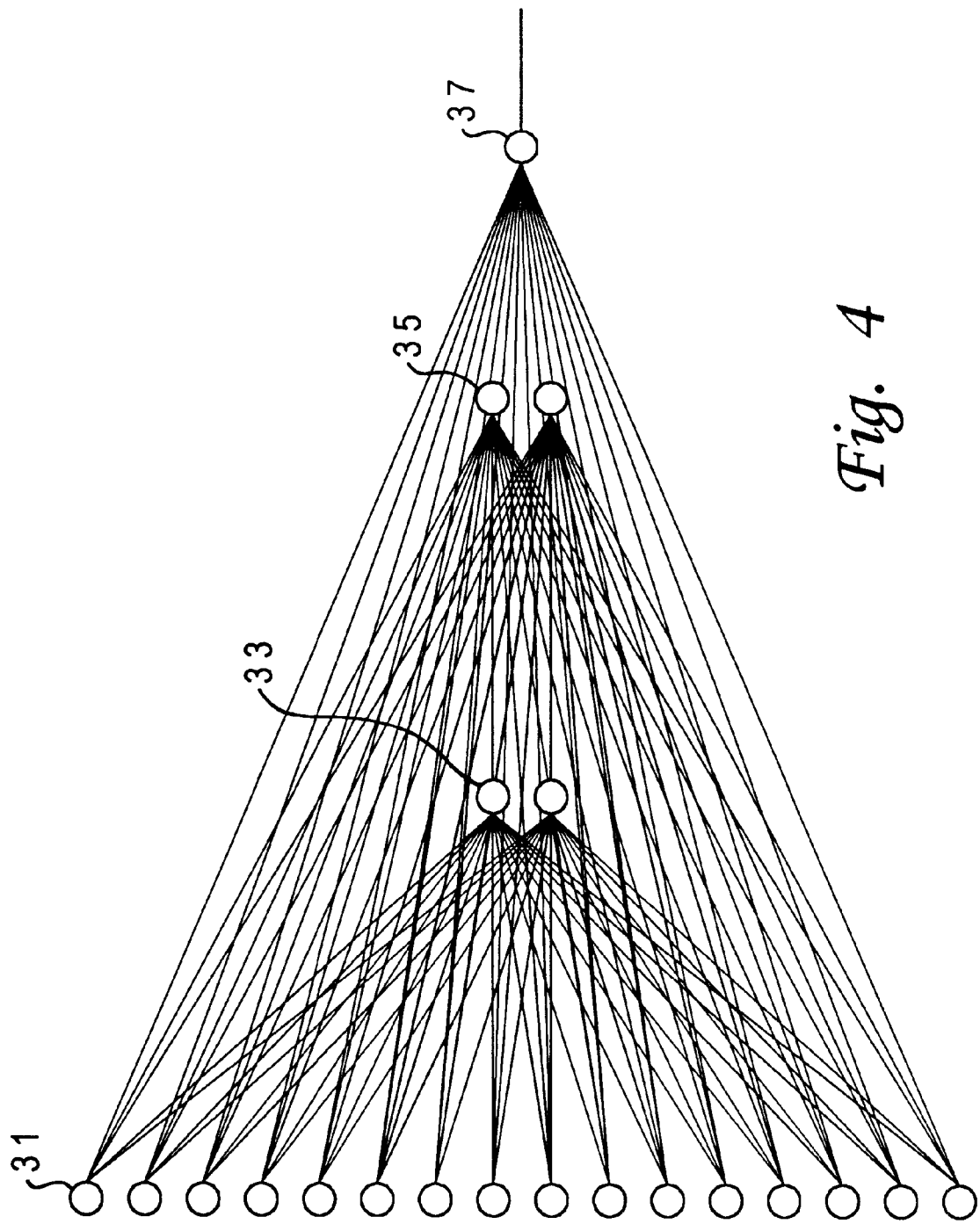

METHOD AND APPARATUS FOR TREATMENT OF SLEEP DISORDER BREATHING EMPLOYING ARTIFICIAL NEURAL NETWORK

This is a continuation of application Ser. No. 08/548,424, filed Oct. 26, 1995.

BACKGROUND OF THE INVENTION

1. Field of the Invention

The present invention relates generally to methods and apparatus for the detection and treatment of sleep disorder breathing. More particularly, the present invention relates to methods and apparatus for detection and treatment of sleep disorder breathing that employ artificial neural networks.

2. Background Information

Disorders of excessive sleepiness present particular health-care concerns. Patients suffering from these disorders experience drowsiness and the need or desire to take naps during the day, and such patients present a history of divorces, employment problems, and automotive accidents.

Among the most common types of sleep disorder breathing is sleep apnea, in which patients experience a partial or complete interruption of air flowing into the lungs for periods exceeding ten seconds. Between 1 and 15 percent of the population is believed to suffer from this condition. Sleep apnea can cause repeated disruption or even cessation of rapid eye movement (REM) sleep, which can cause irritability and a reduction in the ability to memorize information.

There are three recognized types of sleep apnea. Central sleep apnea is characterized by the suspension of all respiratory movement and is generally believed to be neurological in origin. Obstructive sleep apnea is characterized by the collapse of the upper airways during sleep. The third type of sleep apnea is a combination of central and obstructive sleep apnea and is known as mixed apnea.

Obstructive sleep apnea appears to be the most common form of sleep apnea and occurs when the upper respiratory airway of the patient collapses because the tonal activity of the pharyngeal smooth muscle fails to maintain the patency of the airway. Although sporadic and brief airway collapses or obstructive events are not uncommon in the normal adult population, it is considered pathological when obstructive apnea episodes last more than ten seconds and occur over seven-to-ten times per hour.

A symptom indicative of the onset of obstructive sleep apnea is pharyngeal wall vibration, commonly known as snoring. Early detection of pharyngeal wall vibration, and prophylactic treatment of the condition can lead to successful treatment of obstructive sleep apnea. Surgical treatments of obstructive sleep apnea are successful when anatomical abnormalities appear to be the principal cause of obstructive sleep apnea. Non-surgical treatments are successful as well.

One successful non-surgical treatment method is the use of continuous positive airway pressure (CPAP) apparatus. CPAP apparatus administers air or respiratory gas to the patient's airways at a slightly positive pressure level (5 to 20 cmH$_2$O), which maintains the patency of the respiratory airways. The pressure exerted by CPAP apparatus is believed to act as a pneumatic splint for the upper airway. The low-level pressure of the CPAP apparatus is selected after study of the patient in a sleep laboratory. The selected maximum pressure from the sleep study is referred to as prescribed CPAP pressure. Although CPAP apparatus is an effective treatment in 75% of treated patients, the positive airway pressure delivered throughout sleep can cause patient discomfort, including airway pain and dehydration.

An improvement upon CPAP apparatus is described in U.S. Pat. No. 5,458,137, Oct. 17, 1995, to Axe et al., and is known as Adaptive Positive Airway Pressure (APAP) apparatus. APAP apparatus works on the same principle as CPAP apparatus, but does not deliver a single prescribed CPAP pressure. The positive airway pressure administered by APAP is adjusted according to the current needs of the patient, based upon an analysis of the patient's breathing patterns. Principally, if pharyngeal wall vibration is detected, the pressure is increased incrementally. If the patient breathes normally, pressure is decreased. Use of APAP apparatus alleviates some of the patient discomforts with high prescribed CPAP pressures. The ability of APAP apparatus to deliver adequate pressure to the patient is based upon its ability to detect pharyngeal wall vibration or apneic events accurately.

A need exists, therefore, for methods and apparatus for the treatment of sleep disorder breathing that employs detection apparatus having improved ability to detect pharyngeal wall vibration or other apneic events accurately.

SUMMARY OF THE INVENTION

It is a general object of the present invention to provide a method and apparatus for treating sleep disorder breathing having improved ability to accurately detect pharyngeal wall vibration or other apneic events.

This and other objects of the present invention are accomplished by providing an interface or mask for placement over a patient's airway. The interface is coupled to a source of pressurized gas. A respiration-related variable, namely the total pressure in the interface, is measured or sampled. The respiration-related variable is input into an artificial neural network trained to recognize patterns characterizing sleep disorder breathing. Responsive to recognition by the artificial neural network of sleep disorder breathing, pressurized gas is supplied to the patient's airways through the interface.

According to the preferred embodiment of the present invention, a frequency spectrum is obtained from the measured or sampled respiration-related variables. A fast Fourier transform is performed on a selected sample of the measured or sampled respiration-related variables. The frequency components of the frequency spectrum are filtered or normalized prior to being input into the artificial neural network.

According to the preferred embodiment of the present invention, outputs from the artificial neural network over an interval of time are compared to a selected threshold value, and sleep disorder breathing is indicated when the outputs from the artificial neural network exceed the selected threshold value.

Other objects, features, and advantages of the present invention will become apparent with reference to the detailed description of the invention, which follows.

DESCRIPTION OF THE DRAWINGS

FIG. 4 is a schematic diagram of the artificial neural network employed in the apparatus according to the preferred embodiment of the present invention.

DESCRIPTION OF THE PREFERRED EMBODIMENT

Figure 1:
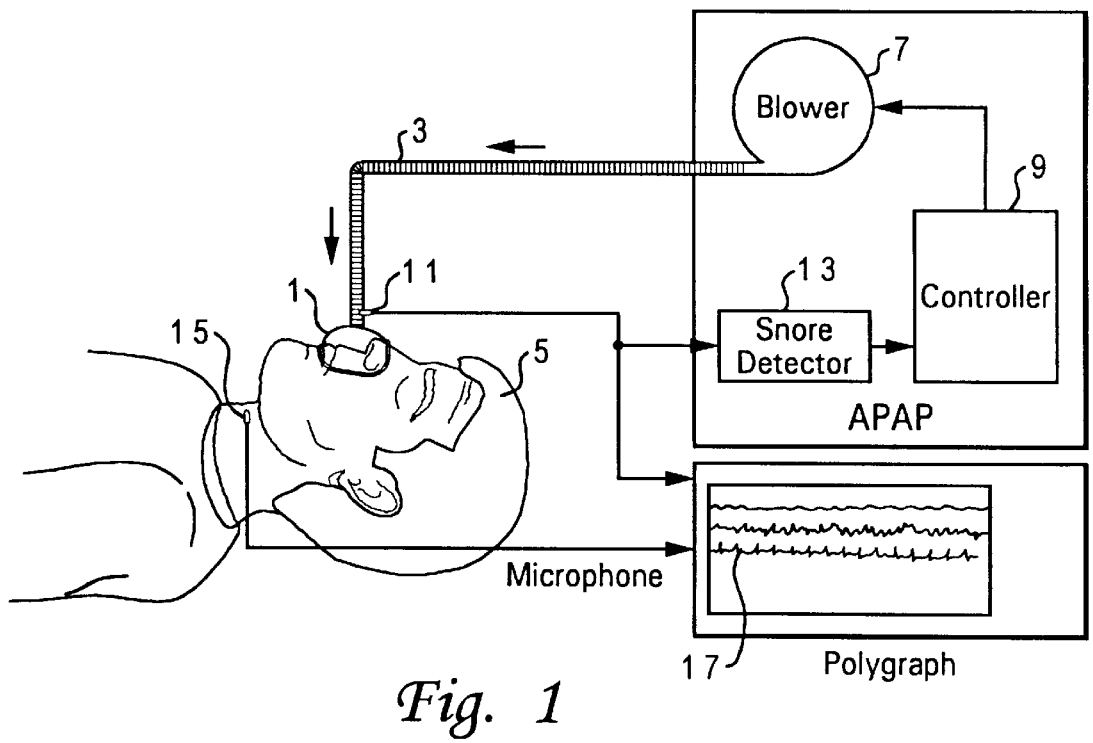
FIG. 1 is a schematic depiction of an adaptive positive airway pressures apparatus according to the present invention.

Referring now to the Figures, and particularly to FIG. 1, an adaptive positive airway pressure (APAP) apparatus according to the present invention is depicted. An interface, in the form of a mask 1 and hose or conduit 3, is placed over the nose and mouth of a patient 5 to deliver pressurized respiratory gas or air to the patient's airway. A blower 7 is connected to the interface and is controlled automatically by a controller 9 to selectively increase the pressure of gas delivered to the patient's airway responsive to indications of sleep disorder breathing. Controller 9 also reduces the pressure delivered through interface 1, 3 by blower 7 responsive to detection of normal breathing.

A pressure transducer 11 is disposed in mask 1 to measure total pressure in mask 1 resulting from respiration and the positive pressure supplied through interface 1, 3 by blower 7. Pressure data from transducer 11 is fed to a snore detector circuit 13, which is coupled to controller 9 for control of blower 7 responsive to detection (or non-detection) of sleep disorder breathing. A microphone 15 is placed on the patient's throat, and the magnitude of breathing sounds is recorded on a strip-chart recorder 17. This data is not necessary for the APAP apparatus according to the present invention, but is useful in training the artificial neural network, as described below. According to the preferred embodiment of the present invention snore detection circuit 13 and algorithm are implemented in software in a personal computer, but can be implemented easily in a microprocessor-based system.

Figure 2:
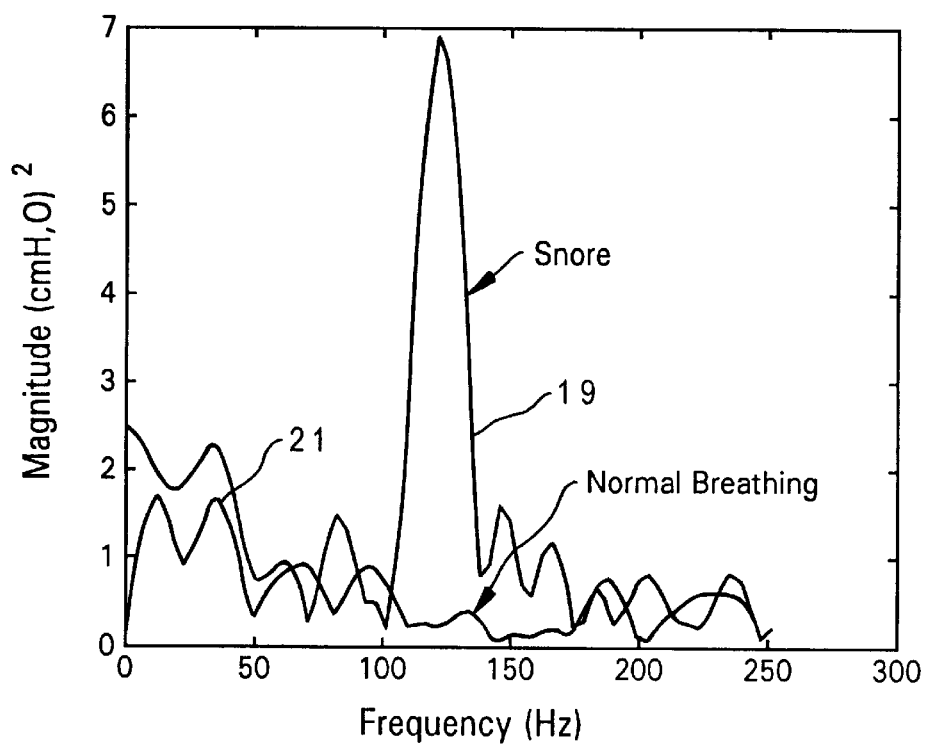
FIG. 2 is a graphical comparison of the frequency spectra of normal breathing compared to breathing involving pharyngeal vibration or snoring.

FIG. 2 is a plot of the frequency spectrum of normal breathing 19 versus the frequency spectrum of sleep disorder breathing 21 characterized by pharyngeal wall vibration or snoring. The data plotted in the graph of FIG. 2 results from pressure measured by the transducer (11 in FIG. 1) in the interface (1, 3 in FIG. 1) of the APAP apparatus depicted in FIG. 1. A fast Fourier transform (FFT) is performed on the pressure data measured by the transducer to obtain the frequency spectra depicted in FIG. 2. As can be seen, there is a marked peak in spectrum 19 corresponding to sleep disorder breathing in the range between 100 and 150 Hz. This is indicative of pharyngeal wall vibration, which is the precursor to most forms of sleep disorder breathing. This peak is not present in spectrum 21 corresponding to normal breathing. Thus, there is a clear distinction between the spectrum corresponding to pharyngeal wall vibration, or sleep disorder breathing, and that corresponding to normal breathing. This distinction is employed to detect sleep disorder breathing in the method and apparatus according to the present invention.

Figure 3:
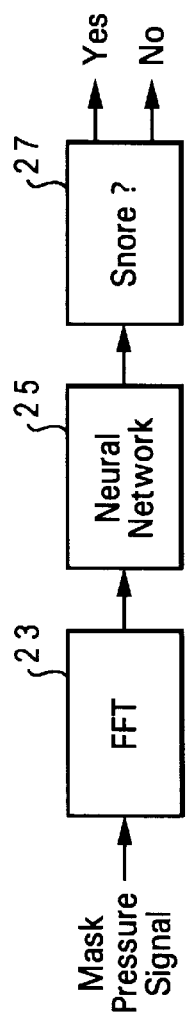
FIG. 3 is a block diagram depicting the apparatus employed in detecting pharyngeal wall vibration according to the preferred embodiment of the present invention.

FIG. 3 is a block diagram of the snore detection apparatus 13 employed by the preferred embodiment of the present invention. The pressure data measured by the transducer in the interface is converted to the frequency domain by performing a fast Fourier transform, as indicated at block 23. The frequency spectrum or data resulting from this step then is normalized and divided into 15 components that are input into an artificial neural network trained to recognize frequency spectra indicative of sleep disorder breathing, as indicated at block 25. In the preferred embodiment of the present invention, if the output of the artificial neural network is 1, snoring is indicated. If the output is 0, snoring is not indicated, at block 27.

FIG. 4 depicts the preferred artificial neural network according to the present invention. The artificial neural network is of the 15-2-2-1 feed-forward topology having full connectivity and 88 weights. This means that the network comprises sixteen input nodes 31, two hidden nodes in the first hidden layer 33, two more hidden nodes 35 in the second hidden layer, and one output node 37. One of the input nodes is always set to −1 and is considered a biased input. Each node or processing unit of the artificial neural network is of the Adaline variety, which has an input vector X having n elements and a weight vector W with n elements. Each element of the input vector is multiplied by its corresponding element of the weight vector and the products are summed and passed through a non-linear sigmoid activation function of the form:

$$a(y) = \frac{1}{1 + \exp(-y)} \quad (1)$$

where y is the summed product of the elements of the input and weight vectors and is given as:

$$y = \sum_{j=1}^{m} W_j X_j \quad (2)$$

where $W_j$ is the weight associated with the branch connecting the $j^{th}$ node to the output node; $X_j$ is the net output from the $j^{th}$ node; and m is the number of nodes connected to the output node.

It has been found that this type of neural network topology strikes a satisfactory balance between accuracy in detecting sleep disorder breathing and efficient use of computational power. A larger or more complex neural network could be selected to enhance accuracy, but the computational power required would be excessive.

According to the preferred embodiment of present invention, the output of the pressure transducer in mask 1 is sampled at 512 Hz. An FFT is calculated every 1/16 second using a 32-point rectangular window. Thus, 32 sample values of the pressure signal are taken and their FFT obtained, and 16 32-point FFTs occur per second. The FFT results in a 32-point frequency spectrum with even symmetry, so that the last 16 components of the spectrum are redundant and may be discarded. The first of the remaining 16 components contains no useful information, and is discarded as well, leaving 15 inputs for the artificial neural network.

Prior to input of the FFT components to the artificial neural network, the components are filtered or normalized so that the average frequency components of normal breathing are of similar magnitude for all patients. This is accomplished by dividing each of the 15 FFT components from a sample window by a value obtained from the equation:

$$z_k = 0.99 z_{k-1} + 0.01 * \bar{x}_k \qquad (3)$$

where $\bar{x}_k$ is the sum of the magnitudes of the 15 components of the frequency spectrum. The value of $\bar{x}_k$ is given by the equation $$\bar{x}_k = \sum_{j=1}^{N} M_{f_j} \qquad (4)$$

where $M_{f_j}$ is the magnitude of the $j^{th}$ frequency component and N is equal to the number of points used to calculate the FFT, in this case 15. The value of $z_k$ obtained from Equation 3 is always similar to the value obtained from the FFT of normal breathing, thus, division of a frequency component by $z_k$ normalizes the frequency component and insures that a frequency component representative of snoring is just that, representative of snoring and not normal breathing.

After filtration or normalization, each of the 15 normalized frequency components is input to nodes 31 of the artificial neural network. A network output of 1 indicates that the neural network detected pharyngeal wall vibration. Noise present in the system can deceive the neural network into recognizing or detecting pharyngeal wall vibration when it is not occurring. However, such noise is generally of brief duration, while pharyngeal wall vibration or snoring generally occurs over one-second intervals and is repetitive. Because several network outputs occur during one second, further processing must occur to avoid spurious indications of pharyngeal wall vibration. Therefore, according to the preferred embodiment of the present invention, the number of positive (indicative of pharyngeal wall vibration) outputs of the artificial neural network over a one-second interval is compared to a threshold value and sleep disorder breathing is indicated and treated only if this threshold is exceeded.

Figure 5:
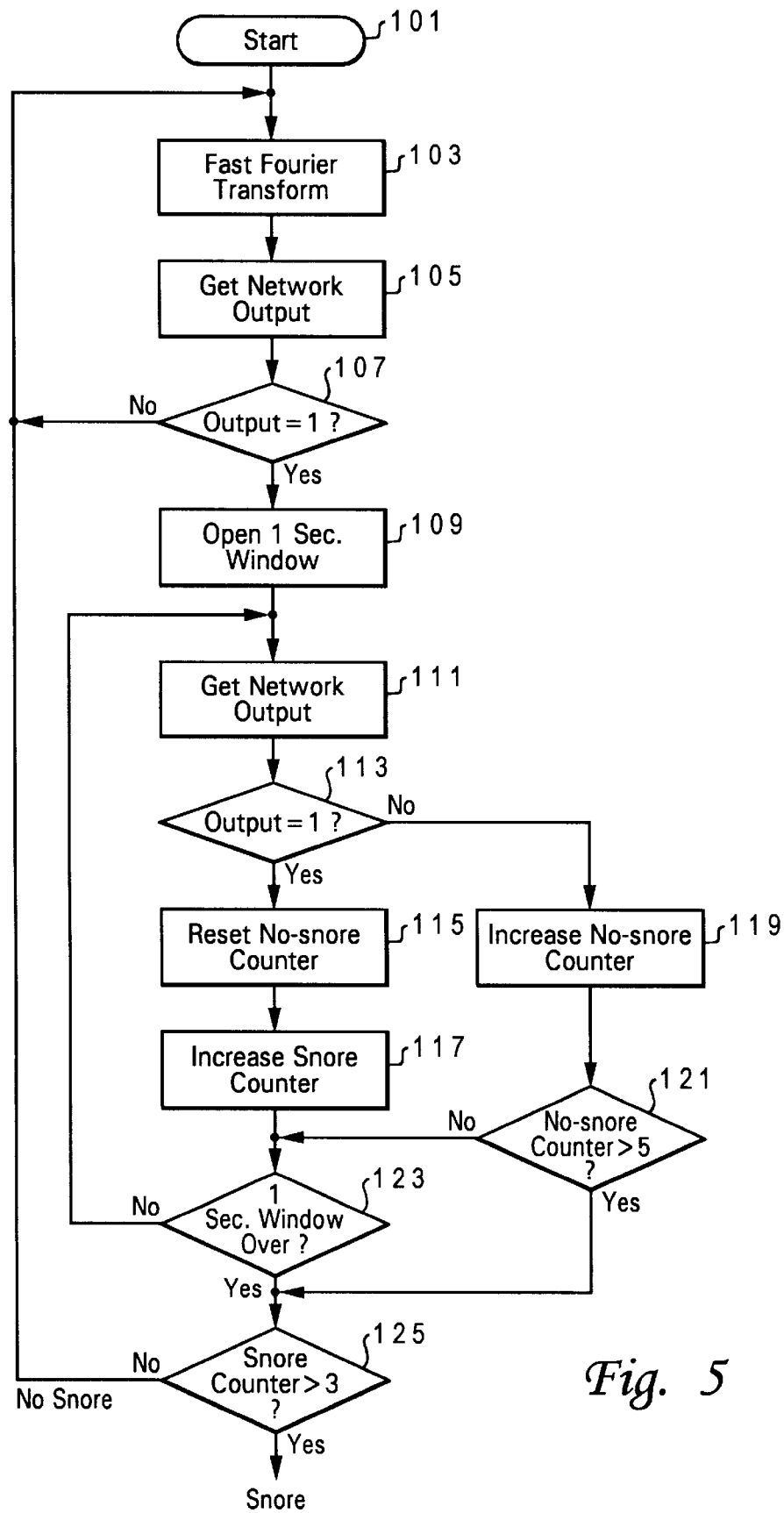
FIG. 5 is a flowchart depicting the process of detection of sleep disorder breathing according to the preferred embodiment of the present invention.

FIG. 5 is a flowchart depicting the process of detection of sleep disorder breathing according to the preferred embodiment of the present invention. At step 101, sampling of pressure data collected by transducer 11 in mask 1 is commenced at 512 Hz. Next, at 103, the FFT is performed on consecutive 32-element ensembles of the pressure data to convert them to the frequency domain and provide a frequency spectrum of the pressure data. Additionally, the normalization described above is performed and the frequency spectrum data is input to the artificial neural network.

At step 105, the network output, either 1 or 0, depending on whether pharyngeal wall vibration is detected, is obtained. At step 107, if the output of the artificial neural network is positive, a one-second window or interval is opened at step 109. If the output is negative or not indicative of sleep disorder breathing, sampling of pressure data continues, and steps 101 through 107 are repeated.

If the one-second window is opened, at step 111, another network output is obtained. At step 113, if the network output is positive, a no-snore counter is reset to 0 and a snore counter is incremented or increased at steps 115 and 117. If the network output is negative, the no-snore counter is incremented or increased at step 119. At step 121, if the no-snore counter indicates that five consecutive negative outputs have been counted by the no-snore counter in the one-second window, steps 103 through 121 are repeated. If fewer than five consecutive negative outputs have been encountered, and the one-second window is not over or closed, steps 111 through 121 are repeated, at step 123.

At step 125, if more than three positive outputs have occurred within the one-second window, snoring or pharyngeal wall vibration is highly probable and snoring is indicated at block 125. Responsive to this indication of pharyngeal wall vibration, controller 9 is activated to control blower 7 to increase the pressure in interface 1, 3 to exert pressure on the patient's airways to counteract pharyngeal wall vibration.

In this detection algorithm, it was assumed that only one pharyngeal wall vibration episode can occur during one breath or within two seconds (the minimum time assumed for one breath). Thus, a one-second window was selected as the interval over which repeated indications of sleep disorder breathing must occur for the apparatus to signal or detect sleep disorder breathing. Because 16 samples per second are input to the artificial neural network, there are 16 opportunities per second for the neural network to yield positive outputs. According to the preferred embodiment of the present invention, if three positive outputs occur in the one-second interval represented by the window, sleep disorder breathing is indicated and steps are taken to counteract pharyngeal wall vibration. If less than three positive outputs occur or more than five consecutive negative outputs occur in the one-second interval, then the process is repeated until sleep disorder breathing is detected.

One aspect of the present invention is the method by which the artificial neural network is trained. The preferred method for training the artificial neural network according to the present invention is with the Delta Learning Rule, which is a supervised training method in which the desired outputs for a given set of input vectors are made available to the artificial neural network while training takes place. During such training, the weights of the nodes of the network are changed by a calculated amount that minimizes the error between the actual output of the network and the desired output. Changes are made in the weights of the nodes until the output of the network resembles the desired output.

A cost function is used as the measure of performance for the output of the network. The objective of training the artificial neural network is to minimize the value of the cost function by adjusting the weights in the nodes. The cost function for the artificial neural network is as follows:

$$E = \tfrac{1}{2}[d - a(y)]^2 \qquad (5)$$

where d is the desired output and a(y) is the actual output of the network.

According to the Delta Learning Rule, the amount by which the weights must be changed to minimize the cost function is given by the formula:

$$\Delta W_j = \eta \delta X_j \qquad (6)$$

where $\eta$ is the learning factor; $W_j$ is weight associated with the branch connecting the $j^{th}$ node to the output node; $X_j$ is the net output from $j^{th}$ node; and $\delta$ is the delta of the output layer. The learning factor is selected by the user and is a positive number less than 1. The learning factor is usually close to 1.0 at the beginning of training and is reduced progressively as training takes place. For the unipolar non-linear function in Equation 1 the value of this delta is given by:

$$\delta = a(y)[1 - a(y)][d - a(y)] \qquad (7)$$

As mentioned earlier, a(y) is the actual output of the network and d is the desired output.

In a network with multiple layers, the weights of the nodes of all layers are adjusted. However, since only the desired output of the overall system is known, there are no desired outputs available for the nodes in the hidden layers. For this reason, a method to reflect the output error to the hidden nodes must be used.

To change the weights in the last hidden layer (the layer previous to the output layer), the effect that the outputs of the nodes in this layer have on the output error is estimated. The contribution of the last hidden layer to the output error is considered to be proportional to the output of the nodes in the last hidden layer, as well as to the weights connecting these nodes to those in the output layer. In essence, this "contribution" becomes the new error that will be used to calculate the adjustment for the weights in this layer.

The weight adjustment for the nodes in hidden layers becomes:

$$\Delta W_{ij} = \eta \gamma_j X_i \tag{8}$$

where:

$$\gamma_j = -\delta W_j a(r) [1-a(r)] \tag{9}$$

and $$r = \sum_{i=1}^{p} W_{ij} X_i \tag{10}$$

where $W_{ij}$ is the weight of connection between the node j in the hidden layer and input node i; $X_i$ is the net output of node i; and p is the number of input nodes.

In this expression, the error term is calculated in the last layer and its weights updated. After having done this, the error of the next layer is calculated and its weights updated. The process continues until the algorithm has reached the first layer. This process is known as "back propagation."

After the weights of the network have been adjusted, a new input is applied to the network and the output is again compared with the desired output. The weights are adjusted with respect to the new input. The process is repeated until the network is capable of producing an output similar to the desired output. Equations 6 and 8 give the optimal change in weights that minimizes the error expressed in the cost function.

Figure 6:
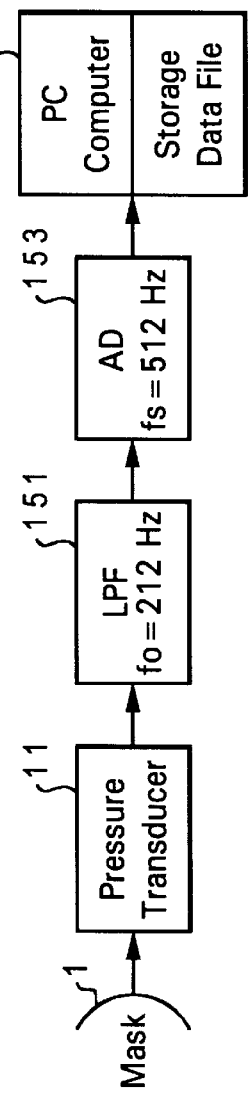
FIG. 6 is a block diagram of the apparatus employed in recording the respiratory data for training the artificial neural network according to the present invention.

FIG. 6 is a block diagram depicting the apparatus employed in gathering data for training the artificial neural network according to the present invention. Pressure transducer 11 in mask 1 is connected by a low-pass filter 151, having a cut-off frequency of 212 Hz, to an analog-to-digital converter 153 with a sampling rate of 512 Hz. Analog-to-digital converter 153 delivers data to a storage data file 155 maintained by a personal computer. The same general apparatus is employed for sampling or measuring data during sleep disorder breathing detection employing the artificial neural network according to the present invention.

Figure 7:
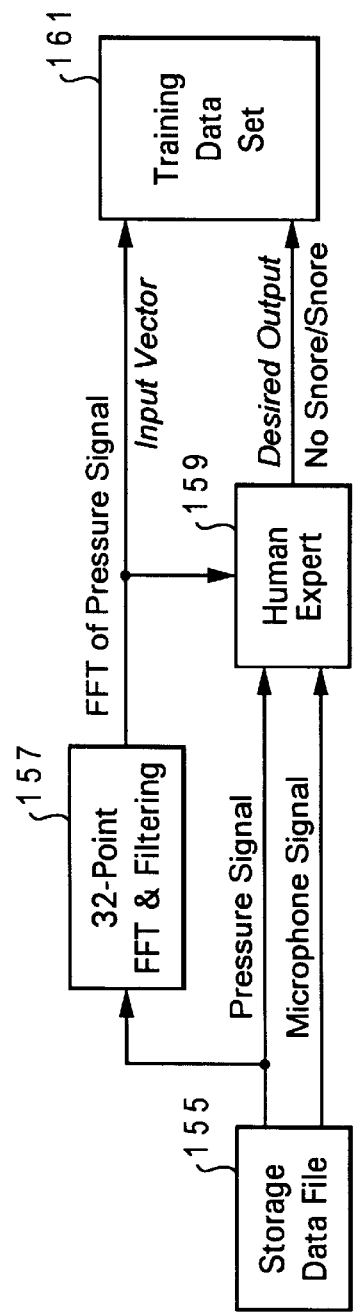
FIG. 7 is a block diagram depicting the apparatus employed in training the artificial neural network according to the preferred embodiment of the present invention.

FIG. 7 is a block diagram depicting the apparatus or elements employed in training the artificial neural network according to the present invention. Sample pressure data is extracted from storage data file 155 and the FFT and filtering described above are performed at 157 to provide the 15 input vectors for the artificial neural network. Simultaneously, or near simultaneously, the pressure data, conventional polysomnograph data, and microphone signal (recorded on a strip-chart recorder) are evaluated by a human expert, at 159, to determine whether the pressure data is actually representative of pharyngeal wall vibration or snoring.

Human expert 159 indicates a desired output (d) corresponding to a set of input vectors. The input vectors and corresponding desired output are stored in a training data set, which is employed in training the artificial neural network according to the present invention.

Figure 8:
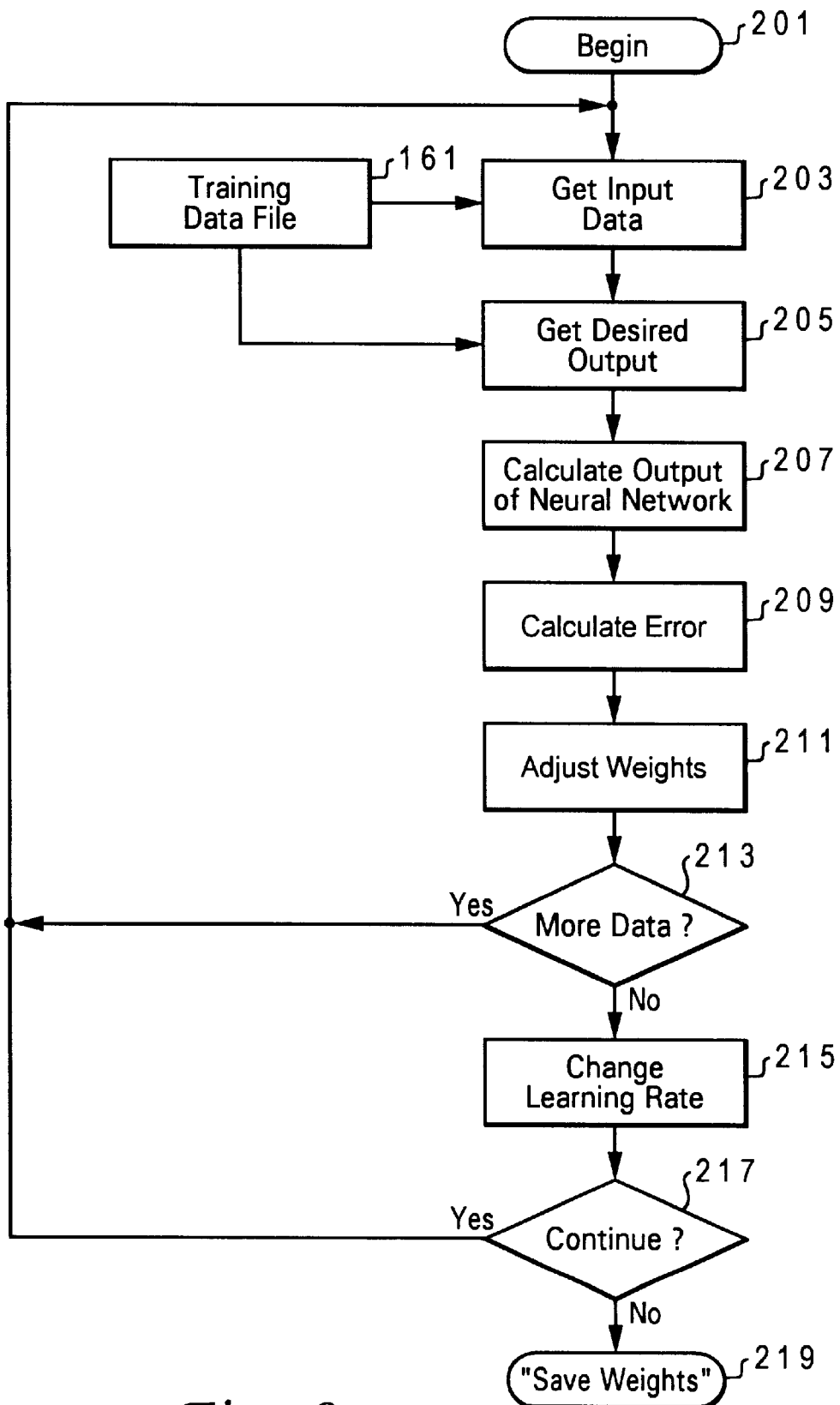
FIG. 8 is a flowchart depicting the steps employed in the training of the artificial neural network according to the present invention.

FIG. 8 is a flowchart depicting the training of the artificial neural network according to the present invention. After commencement of the training routine, at 201, the input data or vectors resulting from the FFT and filtering processes are obtained from training data file 161, at step 203. Similarly, at step 205, the desired outputs, as evaluated by human expert (159 in FIG. 7), are obtained. At step 207, the output of the neural network is calculated or obtained.

At step 209 using Equation 4 and the desired (d) and actual output (a(y)) of the neural network, the error is calculated. At step 211, using Equations 5–10, above, the weights of the artificial neural network are adjusted. At block 213, the decision is made whether to continue training without adjusting the learning rate ($\eta$). If it is advantageous to alter the learning rate, this is done at block 215 and training continues at block 217. If more training is desired without altering the learning rate, then steps 201 through 211 are repeated. At block 217, when the error becomes zero or some other acceptable level, preferably when error ceases to change, the weights as they exist at that point are saved at block 219. Otherwise, the training process continues until the error becomes acceptable. The source code, in the language C, for the FFT and filtering steps, snore detection steps, and training of the artificial neural network is attached in the Appendix.

A principal advantage of the present invention is that it provides an APAP apparatus and method having an improved ability to discriminate between pharyngeal wall vibration and noise present in the system. This results in an APAP apparatus having an improved ability to deliver positive airway pressure to the patient and to reduce the pressure when apneic events are not occurring. Thus, the patient with the sleep disorder breathing experiences more comfort than with CPAP or prior-art APAP apparatus.

The invention has been described with reference to a preferred embodiment thereof. The invention is thus not limited, but is susceptible to variation and modification without departing from the scope of the invention.

© Francisco J. Lopez, 1993

Appendix

```
/*  FILE:    BP9.C
    NAME:    Francisco J. Lopez
    DATE:    October 27th, 1993
    PROGRAM: This program is used to train a neural network
             using the generalized delta rule.
             Networks of up to 4 layers and 20 nodes per layer
             can be trained. This program produces NO plots of
             the results.

NOTE:    This program is to be used in DOS environment    */ include<stdio.h>
include<math.h>
# include<stdlib.h>
# include<io.h>
include<string.h> void getdata();
void readdata();
void calcoutputs();
void adjustweights(float z,int d[15]);
void writeresults();

int Ninp;              /* number of inputs                 */
int Nout;              /* number of outputs                */
int NL;                /* number of layers                 */
int Nn[4];             /* number of nodes in each layer    */
float w[4][4][17][17]; /* connectivity array of network    */
float y[4][21];        /* output of a node                 */
char topfile[13];      /* filename with topology data      */

/****************** START MAIN ************************/
void main()
{   int newold;        /* new or old network topology      */
    int itermax;       /* maximum number of iterations     */
    long int vec;      /* number of training vectors       */
    int h,i,j,k,m;     /* subscript variable               */
    long int l;
    int dummint;       /* dummy variable                   */
    double E;          /* square error                     */
    float Eprev;       /* Error of previous iteration      */
    float error;
    float perE;
    int d[10];         /* desired output read from file    */
    float dummfloat;
    float z;           /* learning factor                  */
    char dumchar;
    char saveans;      /* to save results                  */
    char outfile[13];  /* output file                      */
    char trnfile[13];  /* filename with training data      */
    FILE *trndata;
```

```
FILE *outdata;

/* Select from a new or an old network topology                        */
printf("\nSelect job:    1. training with OLD topology");
printf("\n      2. training with NEW topology");
printf("\n      3. testing with OLD topology");
printf("\nChoose one :  ");
scanf("%d",&newold);
while ((newold < 1) || (newold > 3))
   {  printf("\nERROR! Wrong Selection");
      printf("\nSelect again :    ");
      scanf("%d", &newold);
   }
if (newold == 2)
    getdata();            /* prompt user for topology data       */
else
    readdata();           /* read topology data from file        */ printf("\nEnter the filename with training data:       ");
scanf("%s",trnfile);
trndata = fopen(trnfile,"r");
while (trndata == NULL)
   {     printf("\nERROR! File does not exist. Try again: ");
      scanf("%s",trnfile);
      trndata = fopen(trnfile,"r");
   }

/* Get number of iterations                                            */
if (newold != 3)
{   printf("\nHow many iterations?              ");
    scanf("%d",&itermax);
    printf("\nWrite results in output file? [y/n]    ");
    saveans = getche();
    if (saveans == 'Y') saveans = 'y';
}
else
    itermax = 1;
printf("\nEnter the initial learning factor:        ");
scanf("%f", &z);

if ((saveans == 'y')||(newold == 3))
{   for (j=0;j<=8;j++)
        if (topfile[j] == NULL)
            dummint = j;
    for (j=0;j<=dummint;j++)
        outfile[j] = topfile[j];
    if(newold == 3)
    {   strcat(outfile,".tst");
        outdata = fopen(outfile,"w+");
        fprintf(outdata,"\nDesired      Network    ");
        fprintf(outdata,"\noutput       output       Error");
        fprintf(outdata,"\n-------------------------------");
```

```c
    }
    else
    {   strcat(outfile,".out");
        outdata = fopen(outfile,"w+");
        fprintf(outdata,"\nIteration    Error   Perc.Error");
        fprintf(outdata,"\n----------------------------");
    }
    printf("\nWriting results into file:    %s\n\n",outfile);
}
printf("\nIteration Error      Perc.Error");
printf("\n-------------------------------------");
Eprev = 10E30;

/*************** Start Training Loop ****************** */
for (i=0;i<itermax;i++)
{       E = 0;
    perE = 0;
    l = 0;
    do{     l++;
        /* Read in input from training data file         */
        for(j=0;j<Nn[0]-1;j++)
        {       fscanf(trndata,"%g",&y[0][j]);
        }
        y[0][Nn[0]-1] = -1.;          /* for threshold         */
        /* Calculate output of nodes                     */
        calcoutputs();
        /* Read in desired output from training data file  */
        for(j=0;j<Nn[NL-1];j++)
        {   fscanf(trndata,"%d",&dummint);
            d[j] = dummint;
/*              printf("\noutput= %d\n",d[j]);            */
        }

/* Compute error                                 */
        for(j=0;j<Nn[NL-1];j++)
        {   error = (d[j]-y[NL-1][j])*(d[j]-y[NL-1][j]);
            E = E + error;
            if (error>.25)
                perE = perE+1;
        }
        if (newold != 3)
            adjustweights(z,d);

if (newold == 3)
            for(j=0;j<Nn[NL-1];j++)
        fprintf(outdata,"\n%d %f %G",d[j],y[NL-1][j],error);
        if (kbhit()!=0)
        {   dumchar = getch();
            if (dumchar == 'q')
                break;
            dumchar = 'q';
        }
```

```
        }while(feof(trndata)==0);
        vec = 1;
        rewind(trndata);
        E = E/vec;
        perE = perE/vec;
        if (E > (1.05*Eprev))
        {
            z = z*.9;
            i = i-1;
        }
        else
        {
            if ((saveans == 'y')&&(newold != 3))
              fprintf(outdata,"\n%d    %G %G",i+1,E,perE*100);
            printf("\n%d    %G   %G        %G",i+1,z,E,perE*100);
            Eprev = E;
        }
        if (dumchar == 'q')
            break;

}   /* End of training loop                                        */
    writeresults();
    fclose(outdata);
    fclose(trndata);
    printf("\nNo. of vectors:   %ld\n",vec);
}
/********************** END OF MAIN ********************/

/********************** START READING DATA*************/
void readdata()
{
    int h,i,j,k,l,m;            /* subscript variable                  */
    int dummint;                /* dummy variable                      */
    char filename[20];
    FILE *datafile;

printf("\nEnter the filename with network topology data:");
    scanf("%s",topfile);
    datafile = fopen(topfile,"r");
    while (datafile == NULL)
    {   printf("\nERROR! File does not exist. ");
        printf("Try again    :");
        scanf("%s",topfile);
        datafile = fopen(topfile,"r");
    }
    /* Read in network topology parameters:
        1. number of inputs
        3. number of outputs
        5. number of layers
        6. number of nodes in each layer                               */
```

```
    fscanf(datafile," %d",&Ninp);
    fscanf(datafile," %d",&Nout);
    fscanf(datafile," %d",&NL);
    for (i=0;i<NL;i++)
    {       fscanf(datafile," %d",&dummint);
        Nn[i] = dummint;
    }
    Nn[0] = Nn[0] + 1;      /* because of thresholding          */

/* Read in connectivity array                                */
    for (i=1;i<NL;i++)
        for (j=0;j<Nn[i];j++)
            for (k=0;k<i;k++)               /* source layer     */
                for (l=0;l<Nn[k];l++)       /* source node      */
                    fscanf(datafile,"%f",&w[i][k][j][l]);
    fclose(datafile);
}
/*********************** END OF READDATA ******************/

/*********************** START GETTING DATA ******************/
void getdata()
{
    int h,i,j,k,l,m;            /* subscript variable           */
    int dummint;                /* dummy variable               */

/* if NEW, then get:
        Ninp = number of inputs (features)
        Nout = number of outputs
        NL   = number of layers (max. 4)
        Nn(i)= number of nodes in layer "i"                     */ printf("\nEnter the number of inputs (max. 20):    ");
    scanf("%d", &Ninp);
    printf("\nEnter the number of outputs:    ");
    scanf("%d", &Nout);
    printf("\nEnter the number of layers.");
    printf("\nMax. 4 (including input & output layers):    ");
    scanf("%d", &NL);
    while (NL > 4)
    {       printf("\nMaximum 4 layers!! Try again:    ");
        scanf("%d", &NL);
        printf("\n");
    }
    for (i=1;i<NL-1;i++)
    {   printf("\nNumber of nodes in layer %d:   ",(i+1));
        scanf("%d", &dummint);
        Nn[i] = dummint;
    }
    Nn[0] = Ninp + 1;
    Nn[NL-1] = Nout;
    /* Enter filename where topology will be stored             */
    printf("\nFilename to store network topology:   ");
```

```
    scanf("%s",topfile);

/* assign initial random weights                                        */
    for (i=1;i<NL;i++)                          /* target layer             */
        for (j=0;j<Nn[i];j++)                   /* target node              */
            for (k=0;k<i;k++)                   /* source layer             */
                for (l=0;l<Nn[k];l++)           /* source node              */
                    w[i][k][j][l] = rand()/100.;

}
/*********************** END GETTING DATA ********************/

/*********************** START CALCULATING OUTPUTS ***********/
void calcoutputs()
{
    int h,i,j,k,l,m;            /* subscript variable                       */
    float net[4][10];           /* net input to node                        */
    float dumfloat;

for(j=0;j<NL;j++)
        for(k=0;k<Nn[j];k++)
            net[j][k] = 0.;

/* Calculate the output of the second layer                             */
    for (j=1;j<NL;j++)                          /* "j" dest. layer          */
    {   for (k=0;k<Nn[j];k++)                   /* "k" dest. node           */
        {   for (l=0;l<j;l++)                   /* "l" source layer         */
            for (m=0;m<Nn[l];m++)               /* "m" source node          */
            {   /*printf("\nnet= %f",net[j][k]);
                net[j][k] =net[j][k]+w[j][l][k][m]*y[l][m];
/ * p r i n t f ( " \ n w = % f     y = % f
net=%f",w[j][l][k][m],y[l][m],net[j][k]);*/
            }
            {   dumfloat = net[j][k];
                if (dumfloat<-600) dumfloat = -600;
                y[j][k] = 1/(1.+exp(-dumfloat));
            }
/*          printf("\ny=%f    ",y[j][k]);                                   */
        }
    }
}
/******************** END CALCULATING OUTPUTS ***************/

/******************** START ADJUSTING WEIGHTS ***************/
void adjustweights(float z,int d[10])
{       float dummfloat;
    int h,i,j,k,l,m;                /* subscript variable                   */
    float delta[5][10];             /* delta matrix                         */

/* Calculate negative of gradient                                       */
    for(j=0;j<Nn[NL-1];j++)
        delta[NL-1][j] = (d[j] - y[NL-1][j]);
    for(j=NL-2;j>=1;j--)
```

```c
        for(k=0;k<Nn[j];k++)
        {       dummfloat = 0.;
            for(m=j+1;m<NL;m++)
                for(l=0;l<Nn[m];l++)
                    dummfloat = dummfloat + delta[m][l]*w[m][j][l][k];
            delta[j][k] = (1.-y[j][k])*y[j][k]*dummfloat;
        }
    /* Adjust the weights of the network                              */
    for(j=1;j<NL;j++)
        for(k=0;k<Nn[j];k++)
            for(l=0;l<NL-1;l++)
                for(m=0;m<Nn[l];m++)
                {
                    w[j][l][k][m] = w[j][l][k][m] + z*delta[j][k]*y[l][m];
                }
}
/*********************** END ADJUSTING WEIGHTS ************/

/*********************** START TO WRITE RESULTS ************/
void writeresults()
{
    int h,i,j,k,l,m;              /* subscript variable       */
    FILE *netdata;                /* pointer for topfile      */
    Nn[0] = Nn[0]-1;              /* because of thresholding  */
    netdata = fopen(topfile,"w+");
    fprintf(netdata,"%d ",Ninp);
    fprintf(netdata,"%d ",Nout);
    fprintf(netdata,"%d ",NL);
    for (i=0;i<NL;i++)
        fprintf(netdata,"%d ",Nn[i]);
    fprintf(netdata,"\n");
    Nn[0] = Nn[0] + 1;

for (i=1;i<NL;i++)                          /* target layer   */
    {    for (j=0;j<Nn[i];j++)                  /* target node    */
            for (k=0;k<i;k++)                   /* source layer   */
                for (l=0;l<Nn[k];l++)           /* source node    */
                    fprintf(netdata,"%f ",w[i][k][j][l]);
        fprintf(netdata,"\n");
    }
    fclose(netdata);
}
/*********************** END OF "WRITERESULTS" ************/
```

```
/* FILE:    SNORE36.C
   NAME:    Francisco J. Lopez
   DATE:    1/28/94
   PROGRAM: This program displays and allows an expert to
            classify snores based on the signals being
            displayed. It is to be used to create a training
            file for the network.
*/ include <stdio.h>
include <graphics.h>
# include <stdlib.h>
include <math.h> void timeupdate(char hh, char mm, char ss);
void square(int offset, int dumint);
void screen(char *file, int rate);
void fft();
int calcoutputs(int *N);
void readdata(int *N);

int key(int *f, int flag);
float xtime[128][2];
float xfreq[128][2];
float y[4][17];
float w[4][4][17][17];

/************************** START MAIN ********************/
main()
{     int gdriver=DETECT;
  int gmode;
  int dumint,i,j,k;
  int timecount=0,counter,counter2,counter3,counter4=0;
  int flag,flag2=0,tempj,flag3=1,first=0,new=0;
  int index0=0,index1=0,index2=0,index3=0,wind=1;
  int datainitial[5];
  int tempdata[5];
  int samplerate;
  int set;
  int num=32;
  int save=0,back=1,snore=2,quit=3,cont=4,fast=5,disp=6;
  int f[] = {0, 0, 0, 0, 0, 1, 0};
  int prevpres, prevflow, prevx, base[2];
  int choice;
  int N[5];
  long pos1,pos2;
  float dumfloat;
  float data[6][5];
  float tmp[5];
  float mean[2],meanf[128][2];
  char time[9];
  char temptime[4];
```

```c
char datachange[] = {0,0,0,0,0};
char hh,mm,ss;
char dumchar,dumchar2;
char filename[13];
char filename2[13];
FILE *datafile;
FILE *outfile;
FILE *snorefile;
FILE *savefile;

initgraph(&gdriver,&gmode,"c:\\tc");
do{ cleardevice();
    gotoxy(5,10);
    printf("Enter the name of the data file to be analyzed: ");
    scanf("%s",filename);
    datafile = fopen(filename,"rb");
}while (datafile == NULL);
gotoxy(5,12);
printf("Enter '1' for testing and '0' otherwise      ");
scanf("%d",&choice);
gotoxy(5,14);
for(i=0;i<3;i++)
    temptime[i] = filename[i+9];
temptime[3] = NULL;

if (choice == 1)
{   readdata(&N[0]);
    strcpy(filename2,"snrlg_33.");
    strcat(filename2,temptime);
    filename2[12] = NULL;
    snorefile = fopen(filename2,"w+");
    fprintf(snorefile,"Snore log file:  %s\n",filename2);
}
else
{   strcpy(filename2,"savdt_36.");
    strcat(filename2,temptime);
    filename2[12] = NULL;
    savefile = fopen(filename2,"r");
    if (savefile==NULL)
    {   savefile = fopen(filename2,"w+");
        new = 1;
        strcpy(filename2,"snrdt_36.");
        strcat(filename2,temptime);
        filename2[12] = NULL;
        snorefile = fopen(filename2,"w+");
    }
    else
    {   strcpy(filename2,"snrdt_36.");
        strcat(filename2,temptime);
        filename2[12] = NULL;
        snorefile = fopen(filename2,"r");
        if (snorefile==NULL)
```

```
            printf("Error openning %s\n",filename2);
      }
      strcpy(filename2,"press_36.");
      strcat(filename2,temptime);
      filename2[12] = NULL;
      outfile = fopen(filename2,"w+");
      printf("Writing output data to file:    %s\n",filename2);
}
/******************** Read Time in Data File ************/
fread(&hh,1,1,datafile);
fread(&mm,1,1,datafile);
fread(&ss,1,1,datafile);
samplerate = 512; set = 127;
if((strcmp(filename,"09-09-93")<0)&&(atoi(&filename[7])<4))
{       samplerate = 500;
        set = 49;
}
screen(&filename[0],samplerate);
if (choice==1)
{    fprintf(snorefile,"\nFile:   %s\n\n",filename);
fprintf(snorefile,"Startingtime: %02d:%02d:%02d\n\n",hh,mm,ss);
     fprintf(snorefile,"   Time       snore      noise?\n");
     fprintf(snorefile,"-------------------------------\n");
}
square(535,1);
f[snore] = 0;
flag = 1;
counter = 0;
prevpres = 120;
prevflow = 300;
prevx = 30;
y[0][15] = -1;

do{ for(i=0;i<5;i++)
    {
    /***************** Read Data *********************/
        fread(&datainitial[i],2,1,datafile);
        datachange[i] = 0;
    }
    for(j=0;j<set;j++)
    {   for(i=0;i<5;i++)
        {   if(samplerate==512)
            {   if(i==3)
                datainitial[i]=datainitial[i]+datachange[i]*4;
                else if(i==4)
                datainitial[i]=datainitial[i]+datachange[i]*2;
                else if(i==0)
                datainitial[i]=datainitial[i]+datachange[i]*16;
                else
                datainitial[i]=datainitial[i]+datachange[i];
            }
            else
```

```
            datainitial[i]=datainitial[i]+datachange[i];
        if(samplerate==500)
        {   if (i%2==0)
                tmp[i]=(datainitial[i]-2048)*.025-.193;
            else
                tmp[i] = (datainitial[i]-2048)*.0023-.0133;
        }
        else
        {   tmp[i] = (datainitial[i] - 2048)*.025-.193;
            tmp[1] = (datainitial[1] - 2048)*.0023-.0133;
            tmp[0] = (datainitial[0] - 2048)/2048.;
        }
    }
    if (samplerate==512)
        tmp[3] = -(tmp[4] - tmp[3]);

for(k=0;k<2;k++)
    {   if (counter == 0)
        {   for(i=0;i<128;i++)
                xtime[i][k] = tmp[3+k];
            for(i=0;i<6;i++)
                data[3+k][i] = tmp[3+k];
        }
        for(i=0;i<127;i++)
            xtime[i][k] = xtime[i+1][k];
        for(i=0;i<5;i++)
            data[3+k][i+1] = data[3+k][i];
        data[3+k][0] = tmp[3+k];
        xtime[127][k] = data[3+k][0];
        if (counter==0)
        {       base[k] = xtime[127][k];
        }
/*          printf("%g\n",xtime[127][k]);*/
    }
    /*************** Calculate FFT *******************/
    if(flag==1)
    {   if(((timecount%num)==0)&&(counter!=0))
        {   fft();
            /******** Display FFT *******************/
            setfillstyle(SOLID_FILL,15);
            bar(423,83,615,170);
            bar(423,265,615,350);
            for(dumint=0;dumint<2;dumint++)
            {   setcolor(12);
                dumfloat = 0;
                /**** Filter FFT *******************/
                for(i=0;i<num;i++)
                {   if (first<2)
                        meanf[i][dumint]=xfreq[i][dumint];
                    else
                    {
meanf[i][dumint] = meanf[i][dumint]*.99 + xfreq[i][dumint]*.01;
```

```
                    }
                    if(i!=0)
                        dumfloat=dumfloat+xfreq[i][dumint];
                }
                dumfloat = dumfloat/((num-1)*1.);
                if(first<=4)
                {   mean[dumint] = dumfloat;
                    first++;
                }
                else
mean[dumint]=mean[dumint]*.99 + dumfloat*.01;

if(f[disp]==1)
                {   gotoxy(40,dumint+20);
                    printf("%f ",mean[dumint]);
                }
                setcolor(12);
                for(i=0;i<num;i++)
                {
xfreq[i][dumint] = xfreq[i][dumint]/mean[dumint];
                    if (i<(num/2))
                    {   dumfloat = xfreq[i][dumint]*8;
                        moveto(455+i*8,349-dumint*180);
                        if(dumfloat>80) dumfloat = 80;
lineto(455+i*8,349-dumfloat-dumint*180);
                    }
                }
                setcolor(0);
                for(i=0;i<(num/2);i++)
                {
dumfloat = (meanf[i][dumint]*8)/mean[dumint];
                        if(dumfloat>80) dumfloat = 80;
                        if(i==0)
 moveto(455+i*8,349-dumint*180-dumfloat);
 lineto(455+i*8,349-dumint*180-dumfloat);
                }
            }
        }
        /*********** Move Fast/Slow *******************/
        if ((f[fast] == 0)&&((counter%5)==0))
            key(f,flag);
        /*********** Feed FFT into ANN ****************/
        if (choice==1)
        {   for (i=1;i<16 ;i++)
            {   dumint = i*(num/2)/16;
                y[0][i-1] = xfreq[dumint][1];
            }
            f[snore] = calcoutputs(N)/1;
        }
        else
        /*********** Save Vectors into File ***********/
        {   if(f[save]==1)
```

```
                {
                    if((timecount%1)==0)
                    {       fprintf(outfile," %f",tmp[4]);
                    }
                }
            }
            /*********** Final Decision ******************/
            if (f[disp]==1)
            {   gotoxy(3,22);
                for (i=5;i<10;i++)
                    printf("%4.3f   ",y[0][i]);
                printf(" %d ",f[snore]);
            }
            i = (counter%7000)/20;
            if(f[snore]==1)
            {       if (index3 == 0)
                {   index2 = 1;
                    index1++;
                }
                counter2=0;
                if (f[disp]==1)
                {   gotoxy(3,20);
                    printf(" %d   ",index1);
                }
            }
            if (index2==1)
            {   index0++;
                putpixel(30+i,208,9);
                putpixel(30+i,213,9);
                counter2++;
            }
            if(((index0>550)||(counter2>130))&&(f[snore]==0))
            {   counter4++;
                index2=0;
            }
            if(((index0>500)||(counter2>130))&&(counter4>25))
            {   if((index1>=128)&&((wind>3)||(counter>4000)))
                {       setcolor(4);
                        outtextxy(30+i,217,"x");
                        if (choice == 1)
   fprintf(snorefile,"%02d:%02d:%02d    %d\n",hh,mm,ss,index1);
                        index3 = 1;
/*                      getch();*/
                }
                else if
((index1>=64)&&((wind>3)||(counter>4000)))
                {       setcolor(4);
                        outtextxy(30+i,217,"o");
                        if (choice == 1)
   fprintf(snorefile,"%02d:%02d:%02d    %d\n",hh,mm,ss,index1);
                }
```

```
            else    index3 = 0;
        index1 = 0;
        index0 = 0;
        counter3 = (samplerate*3)/4;
        counter4 = 0;
    }
    if (index3 == 1)
    {   counter3--;
        index2 = 0;
    }
    if (counter3 <0)
        index3 = 0;
    if((timecount%samplerate)==0)
    {   ss = ss+1;
        if(ss>59)
        {   ss = 0;
            mm = mm + 1;
            if(mm>59)
            {   mm = 0;
                hh = hh + 1;
                if(hh>24)
                    hh = 1;
            }
        }
        setfillstyle(SOLID_FILL,7);
        setcolor(0);
        bar(490,434,625,455);
        settextstyle(SANS_SERIF_FONT,HORIZ_DIR,0);
        settextjustify(1,0);
        time[0] = NULL;
        sprintf(time,"%02d:%02d:%02d",hh,mm,ss);
        outtextxy(555,455,time);
        timecount = 0;
    }
}
/*************** Display Pressure Signal **********/
i = (counter%7000)/20;
if ((counter%4)==0)
{   setcolor(14-12*flag+f[snore]*2*flag);
    if((prevx-(30+i))>0) prevx = 29+i;
    moveto(prevx,prevflow);
    prevflow = 307-(xtime[127][0]-base[0])*10;
    if (prevflow >356) prevflow = 356;
    else if (prevflow <257) prevflow = 257;
    lineto(30+i,prevflow);

moveto(prevx,prevpres);
    prevpres = 125+(xtime[127][1]-base[1])*8;
    if (prevpres > 178) prevpres = 178;
    else if (prevpres < 79) prevpres = 79;
    lineto(30+i,prevpres);
    prevx = 30 + i;
```

```
                                                                        90
            if(flag==1)
            {   putpixel(30+i,210,10+f[snore]*2);
                putpixel(30+i,211,10+f[snore]*2);
            }
            if(flag2==1)
            {   /*settextstyle(DEFAULT_FONT,HORIZ_DIR,2);*/
                setcolor(14);
outtextxy(34+i,170,"|");outtextxy(30+i,348,"|");
                setcolor(15);
outtextxy(32+i,170,"|");outtextxy(28+i,348,"|");
            }
        }
        if ((counter%1)==0)
        {   if(samplerate==512)
            {   dumint =  435-tmp[0]*30;
                putpixel(30+i,dumint,14-flag*14);
                if(f[disp]==1)
                {   gotoxy(3,21);
                    printf("%f ",tmp[0]);
                }
            }
        }
    }
    /*************** Read New Data ********************/
    for(i=0;i<5;i++)
        fread(&datachange[i],1,1,datafile);
    /*************** End of "screen" ******************/
    if(((counter%7000)==0)||(feof(datafile)!=0))
    {   if(flag==1)
        {   pos1 = ftell(datafile);
            temptime[0] = hh;
            temptime[1] = mm;
            temptime[2] = ss;
            for(i=0;i<5;i++)
                tempdata[i] = datainitial[i];
            tempj=j;
            if(f[cont] == 0) getch();
            setfillstyle(SOLID_FILL,15);
            bar(13,79,397,178);
            bar(13,257,397,356);
            bar(13,401,397,463);
            setfillstyle(SOLID_FILL,7);
            bar(13,201,397,220);
        }
        if (flag == 0)
        {   fseek(datafile,pos1,SEEK_SET);
            hh = temptime[0];
            mm = temptime[1];
            ss = temptime[2];
            for(i=0;i<5;i++)
                datainitial[i] = tempdata[i];
            j=tempj;
            if(f[cont] == 0) getch();
```

```
                }
                counter = 0;
                wind ++;
                flag = abs(flag-1);
                flag2=0;
        }
        counter++;
        if (flag==1) timecount++;
}
/****************** Move Back ***********************/
if ((f[back] == 1)&&(flag == 1))
{       pos2 = ftell(datafile);
        do{ dumchar = getch();
                dumchar2 = getch();
                i = counter/20;
                setcolor(15);
                outtextxy(30+i,170,"|");outtextxy(30+i,348,"|");
                setcolor(14);
                outtextxy(28+i,170,"|");outtextxy(28+i,348,"|");
                putpixel(30+i,210,7);
                putpixel(29+i,210,7);
                putpixel(30+i,211,7);
                putpixel(29+i,211,7);
                /*********** Move Clock Back ******************/
                for(k=j;k!=0;k--)
                {       timecount--;
                        counter--;
                        if(timecount==0)
                        {       ss = ss - 1;
                                if(ss<0)
                                {       ss = 59;
                                        mm = mm-1;
                                        if(mm<0)
                                        {       mm = 59;
                                                hh = hh-1;
                                                if(hh<0) hh = 11;
                                        }
                                }
                                setfillstyle(SOLID_FILL,7);
                                setcolor(0);
                                bar(490,434,625,455);
                                settextjustify(1,0);
                                time[0] = NULL;
                                sprintf(time,"%02d:%02d:%02d",hh,mm,ss);
                                outtextxy(555,455,time);
                                timecount = samplerate;
                        }
                        pos2 = pos2 - 5L;
                }
                pos2 = pos2 - 10L;
                j = set;
                fseek(datafile,pos2,SEEK_SET);
```

```c
            if((counter == 1)||(dumchar2 == 'M'))
            {   f[back] = 0;
                square(148,f[back]);
                flag2=1;
                break;
            }
        }while(f[back]==1);
    }
    if(flag3==1)
    {   for(k=0;k<2;k++)        base[k] = xtime[127][k];
        flag3 = 0;
    }
    /***************** Read Keyboard *******************/
    if (kbhit() != 0)
        flag3 = key(&f[0],flag);
    if(f[quit]==1)
        break;      /*Quit*/
  }while(feof(datafile)==0);
  if (choice==1)
fprintf(snorefile,"\nEnding time: %02d:%02d:%02d\n\n",hh,mm,ss);
  getch();
  dumchar = dumchar;
  fcloseall();
  closegraph();
}
/********************** END OF MAIN ******************/

/************************ START OF KEY ****************/
int key(int *f,int flag)
{   char dumchar;
  int save=0,back=1,snore=2,quit=3,cont=4,fast=5,disp=6;
  int flag3;

dumchar = getch();
  dumchar = toupper(dumchar);
  switch(dumchar)
  {   case ' ':if (flag == 1)
            {   *(f+ fast)=abs(*(f+fast)-1);/*space(Fast/Slow*/
                square(535,*(f+fast));
                square(577,abs(*(f+fast)-1));
            }
            break;
      case 'S':*(f+save) = abs(*(f+save)-1);
            square(55,*(f+save));
            break;
      case 'Q':*(f+quit)=1;
            square(334,1);
            break;
      case 'B':*(f+back) = abs(*(f+back)-1);   /* Back/Forward */
            square(148,*(f+back));
            break;
```

```
            case 'N':*(f+snore) = abs(*(f+snore)-1);
                square(246,*(f+snore));
                break;
            case 'X':flag3 = 1;
                return(flag3);
            case 'C':*(f+cont) = abs(*(f+cont)-1);
                square(420,*(f+cont));
                break;
            case 'D':*(f+disp) = abs(*(f+disp)-1);
                break;
            case NULL: dumchar = getch();
                switch(dumchar)
                {       case 'P':*(f+snore) = 0;         /*down      */
                            square(246,0);
                            break;
                        case 'H':*(f+snore) = 1;         /*up        */
                            square(246,1);
                            break;
                        case 'M':*(f+back) = 0;          /*right     */
                            square(148,0);
                            break;
                        case 'K':*(f+back) = 1;          /*left      */
                            square(148,1);
                }
    }
}
/************************* END OF KEY *********************/

/************************* START OF FFT *******************/
void fft()
{     int mmax, istep, m, n=32, i, j,k;
    float theta, wr, wi, tempr, tempi, temp;
    float rd[128],id[128];

for(k=0;k<2;k++)
    {   for(i=0;i<n;i++)
        {   rd[i] = xtime[i][k];
            id[i] = 0;
        }
        j = 1;
        for (i=1;i<=n;i++)
        {   if (i<j)
            {   temp = rd[i-1];
                rd[i-1] = rd[j-1];
                temp = id[i-1];
                id[i-1] = id[j-1];
                id[j-1] = temp;
            }
            m = n/2;
            while(j>m)
            {   j = j - m;
                m = floor((m+1)/2);
```

```
            }
         j = j + m;
      }
      mmax = 1;
      while(mmax<n)
      {   istep = 2*mmax;
          for(m=1;m<=mmax;m++)
          {   theta = 3.1416*(m-1)/mmax;
              wr = cos(-theta);
              wi = sin(-theta);
              for(i=m;i<=n;i=i+istep)
              {   j = i+mmax;
                  tempr = wr*rd[j-1] - wi*id[j-1];
                  tempi = wr*id[j-1] + wi*rd[j-1];
                  rd[j-1] = rd[i-1] - tempr;
                  id[j-1] = id[i-1] - tempi;
                  rd[i-1] = rd[i-1] + tempr;
                  id[i-1] = id[i-1] + tempi;
              }
          }
          mmax = istep;
      }
      for(i=0;i<n;i++)
          xfreq[i][k] = sqrt(rd[i]*rd[i] + id[i]*id[i]);
   }
}
/************************** END OF FFT *******************/

/************************** START OF SQUARE ****************/
void square(int offset, int dumint)
{       if(dumint == 1) setcolor(8);
  else              setcolor(7);
  moveto(offset,17);  lineto(40+offset,17); lineto(40+offset,32);
  if(dumint == 1) setcolor(15);
  else              setcolor(7);
  moveto(40+offset,32);  lineto(offset,32); lineto(offset,17);
}
/************************** END OF SQUARE ****************/

/************************** START OF SCREEN ****************/
void screen(char *file, int rate)
{     int gmode, gdriver = DETECT;
  int maxx, maxy;
  char dumstr[5];

initgraph(&gdriver,&gmode,"c:\\tc");
  maxx = getmaxx();
  maxy = getmaxy();

setbkcolor(0);
  setfillstyle(SOLID_FILL,15);
  bar(0,0,maxx,maxy);
```

```
setfillstyle(SOLID_FILL,7);
setcolor(8);
bar3d(8,5,maxx-8,45,4,1);        rectangle(14,9,maxx-14,41);
bar3d(8,52,402,191,4,1);         bar3d(410,52,maxx-8,191,4,1);
bar3d(8,196,402,225,4,1);        bar3d(410,196,maxx-8,225,4,1);
bar3d(8,230,402,369,4,1);        bar3d(410,230,maxx-8,369,4,1);
bar3d(8,374,402,476,4,1);        bar3d(410,374,maxx-8,476,4,1);

rectangle(12,56,398,75);         rectangle(414,56,maxx-13,75);
rectangle(12,200,398,221);       rectangle(414,200,maxx-13,221);
rectangle(12,234,398,251);       rectangle(414,234,maxx-13,251);
rectangle(12,378,398,397);       rectangle(414,378,maxx-13,472);

setfillstyle(SOLID_FILL,15);
bar3d(12,78,398,179,0,1);        bar3d(414,78,maxx-13,179,0,1);
bar3d(12,256,398,357,0,1);       bar3d(414,256,maxx-13,357,0,1);
bar3d(12,400,398,464,0,1);

settextstyle(DEFAULT_FONT,HORIZ_DIR,1);
setcolor(0);
outtextxy(425,395,"FILE:");
outtextxy(425,410,"S.RATE:       Hz");
outtextxy(425,445,"TIME:");
outtextxy(495,395,file);
outtextxy(495,410,itoa(rate,dumstr,10));

settextjustify(1,1);
outtextxy(205,66,"EXTERNAL PRESSURE");
outtextxy(519,66,"FFT PRESSURE");
outtextxy(205,243,"FLOW");
outtextxy(519,243,"FFT FLOW");
outtextxy(205,388,"MICROPHONE");
outtextxy(519,211,"  SNORE      NO SNORE");
settextjustify(0,1);
outtextxy(45,25,"- Save");
outtextxy(138,25,"- Back");
outtextxy(231,25,"- snore");
outtextxy(324,25,"- Quit");
outtextxy(412,25,"- Cont.");
outtextxy(525,25,"- Fast Slow");
settextjustify(2,1);
settextstyle(DEFAULT_FONT,HORIZ_DIR,2);
outtextxy(45,25,"S");
outtextxy(138,25,"B");
outtextxy(231,25,"N");
outtextxy(324,25,"Q");
outtextxy(412,25,"C");
outtextxy(525,25,"bar");

setcolor(15);
moveto(14,9);      lineto(14,41);     lineto(maxx-14,41);
moveto(12,56);     lineto(12,75);     lineto(398,75);
```

```
                                                                    96
    moveto(414,56);       lineto(414,75);      lineto(maxx-14,75);
    moveto(12,200);       lineto(12,221);      lineto(398,221);
    moveto(414,200);      lineto(414,221);     lineto(maxx-14,221);
    moveto(12,234);       lineto(12,251);      lineto(398,251);
    moveto(414,234);      lineto(414,251);     lineto(maxx-14,251);
    moveto(12,378);       lineto(12,397);      lineto(398,397);
    moveto(414,378);      lineto(414,472);     lineto(maxx-14,472);

setcolor(0);
    setfillstyle(SOLID_FILL,4);       circle(440,211,5);
        floodfill(442,211,0);
    setfillstyle(SOLID_FILL,10);      circle(525,211,5);
        floodfill(525,211,0);
}
/********************* END OF SCREEN ******************/

/************************ START OF READDATA **************/
void readdata(int *N)
{     int dumint,i,j,k,l;
    char topfile[13];
    char filename[20];
    FILE *datafile;

do{ printf("Enter the file name with the network topology  ");
        scanf("%s",topfile);
        strcpy(filename,"d:\\nih_data\\");
        strcat(filename,topfile);
        datafile = fopen(filename,"r");
    }while (datafile == NULL);

fscanf(datafile,"%d",&dumint);
    fscanf(datafile,"%d",&dumint);
    fscanf(datafile,"%d",&dumint);
    *N = dumint;
    for (i=1;i<=*N;i++)
    {   fscanf(datafile,"%d",&dumint);
        *(N+i) = dumint;
    }
    *(N+1) = *(N+1) + 1;    /* because of thresholding        */

/* Read in connectivity array                             */
    for (i=1;i<*N;i++)
        for (j=0;j<*(N+i+1);j++)
            for (k=0;k<i;k++)
                for (l=0;l<*(N+k+1);l++)
                    fscanf(datafile,"%f",&w[i][k][j][l]);
    fclose(datafile);
}
/********************** END OF READDATA ****************/

/*********************** START OF CALCOUTPUTS **********/
int calcoutputs(int *N )
```

```
{    int j,k,l,m;
 float net[5][15];
 float dumfloat;
 for(j=1;j<*N;j++)
      for(k=0;k<*(N+j+1);k++)
           net[j][k] = 0;
 for (j=1;j<*N;j++)
 {       for (k=0;k<*(N+j+1);k++)
        {       for(l=0;l<j;l++)
                for (m=0;m<*(N+l+1);m++)
                   net[j][k] = net[j][k] + w[j][l][k][m]*y[l][m];
/*                     if (j==*N-1)
           y[j][k] = net[j][k];
       else                                                      */
       {   dumfloat = net[j][k];
           if (dumfloat < -600) dumfloat = -600;
           y[j][k] = 1/(1.+exp(-dumfloat));
       }
    }
 }
/*    printf("%g",floor(y[*N-1][0]+.5)/1);*/
 return(floor(y[*N-1][0]+.5));
}
/*********************** END OF CALCOUTPUTS ************/
```

We claim:

1. A method of treating sleep disorder breathing, the method comprising the steps of:

placing an interface over a patient's airway, the interface coupled to a source of pressurized gas;

measuring a respiration-related variable in the interface;

inputting frequency data from the respiration-related variables into an artificial neural network trained to recognize patterns characterizing sleep disorder breathing;

responsive to recognition by the artificial neural network of sleep disorder breathing, supplying pressurized gas to the patient's airway through the interface.

2. The method according to claim 1 wherein the step of measuring respiration-related variables includes the step of obtaining a frequency spectrum from the measured respiration-related variables.

3. The method according to claim 1 further comprising the step of:

comparing a number of outputs of the artificial neural network over a selected interval to a selected threshold value and indicating sleep disorder breathing only if the number of outputs of the artificial neural network indicative of sleep disorder breathing exceeds the selected threshold value.

4. The method according to claim 1 further comprising the step of normalizing the measured respiration-related variable prior to inputting them into the artificial neural network.

5. The method according to claim 1 wherein the respiration-related variable is the pressure in the interface.

6. A method of treating sleep disorder breathing, the method comprising the steps of:

placing an interface over a patient's airway, the interface coupled to a source of pressurized gas;

measuring respiration-related variables in the interface;

obtaining a frequency spectrum from the measured respiration-related variables, the frequency spectrum including at least one frequency component;

inputting the frequency component of the frequency spectrum into an artificial neural network trained to recognize patterns characteristic of sleep disorder breathing;

responsive to output from the artificial neural network indicative of sleep disorder breathing, supplying pressurized gas to the patient's airway through the interface.

7. The method according to claim 6 wherein the step of obtaining a frequency spectrum from the measured respiration-related variables comprises performing a fast Fourier transform on a selected group of sample of measured respiration-related variables.

8. The method according to claim 6 further comprising the step of:

comparing a number of outputs of the artificial neural network over a selected interval to a selected threshold value and indicating sleep disorder breathing only if the number of outputs of the artificial neural network indicative of sleep disorder breathing exceeds the selected threshold value.

9. The method according to claim 6 further comprising the step of:

normalizing the components of the frequency spectrum prior to inputting them into the artificial neural network.

10. The method according to claim 6 wherein the respiration-related variables are the pressure in the interface.

11. A method of treating sleep disorder breathing, the method comprising the steps of:

placing an interface over a patient's airway, the interface coupled to a source of pressurized gas;

periodically sampling pressure in the interface;

periodically inputting frequency data from the sample of pressure in the interface into an artificial neural network trained to recognize patterns characterizing sleep disorder breathing, the artificial neural network producing an output for each sample of pressure input;

comparing the number of outputs indicating sleep disorder breathing to a selected threshold value, sleep disorder breathing being indicated if the number of outputs exceeds the threshold value; and responsive indicated sleep disorder breathing, supplying pressurized gas to the patient's airway through the interface.

12. The method according to claim 11 further including the step of obtaining a frequency spectrum from the measured respiration-related variables.

13. The method according to claim 12 further comprising the step of:

normalizing the components of the frequency spectrum prior to inputting them into the artificial neural network.

14. An apparatus for treatment of sleep disorder breathing comprising:

an interface for placement over a patient's airway, the interface coupled to a source of pressurized gas;

means for measuring respiration-related variables in the interface;

means for inputting frequency data from the respiration-related variables into an artificial neural network trained to recognize patterns characterizing sleep disorder breathing;

means for supplying pressurized gas to the patient's airway through the interface responsive to recognition by the artificial neural network of sleep disorder breathing.

15. The apparatus according to claim 14 further comprising:

means for obtaining a frequency spectrum from the measured respiration-related variables.

16. The apparatus according to claim 14 further comprising:

means for comparing a number of outputs of the artificial neural network over a selected interval to a selected threshold value and indicating sleep disorder breathing only if the number of outputs of the artificial neural network indicative of sleep disorder breathing exceeds the selected threshold value.

17. The apparatus according to claim 14 further comprising:

means for normalizing the measured respiration-related variables prior to inputting them into the artificial neural network.

* * * * *